US012618824B2

(12) United States Patent
Kim et al.

(10) Patent No.: US 12,618,824 B2
(45) Date of Patent: May 5, 2026

(54) REAL-TIME WATER QUALITY MONITORING DEVICE AND METHOD

(71) Applicant: GEOGRID INC., Seongnam-si (KR)

(72) Inventors: Kihyun Kim, Namyangju-si (KR); Jiha Yi, Seoul (KR)

(73) Assignee: GEOGRID INC., Seongnam-si (KR)

( * ) Notice: Subject to any disclaimer, the term of this patent is extended or adjusted under 35 U.S.C. 154(b) by 386 days.

(21) Appl. No.: 18/386,366

(22) Filed: Nov. 2, 2023

(65) Prior Publication Data

US 2025/0116646 A1 Apr. 10, 2025

(30) Foreign Application Priority Data

Oct. 6, 2023 (KR) ........................ 10-2023-0133303

(51) Int. Cl.
*G01N 33/18* (2006.01)
(52) U.S. Cl.
CPC ............................... *G01N 33/1886* (2013.01)
(58) Field of Classification Search
CPC .... G01N 33/18; G01N 33/1886; G01D 11/24; G01D 11/245; G01D 2001/205; G01D 2001/2035; G01D 2001/2064
USPC ............................................... 73/431, 863.61
See application file for complete search history.

(56) References Cited

U.S. PATENT DOCUMENTS

2009/0090663 A1* 4/2009 Hirata .................. B01D 65/102
210/93

FOREIGN PATENT DOCUMENTS

| JP | 5308233 | B2 | 10/2013 | |
|----|---------|----|---------|--|
| KR | 200410068 | Y1 * | 3/2006 | ............. G01N 33/18 |
| KR | 101707282 | B1 * | 2/2017 | ............. G01D 21/02 |
| KR | 10-2202027 | B1 | 1/2021 | |
| KR | 102556038 | B1 * | 7/2023 | ......... G01N 33/0036 |

OTHER PUBLICATIONS

Machine translation of KR 101707282 B1 (Year: 2017).*
Machine translation of KR 102556038 (Year: 2023).*
Machine translation of KR 200410068 Y1 (Year: 2004).*

* cited by examiner

*Primary Examiner* — Nathaniel J Kolb
(74) *Attorney, Agent, or Firm* — Sughrue Mion, PLLC

(57) ABSTRACT

A real-time water quality monitoring device may include: a pipe module having the shape of a pipe along which water flows; a first chamber module connected to the pipe module and having a pair of first opening and closing parts openable and closable according to a control signal; a second chamber module connected to the first chamber module through a second opening and closing part openable and closable so that if the second opening and closing part is open in the state where the pair of first opening and closing parts is closed, the second chamber module acquires measurement data related to water quality from the water accommodated in the first chamber module; and a control module for generating the control signal according to an external input, producing water quality information using the measurement data, and transmitting the water quality information to at least one predetermined management terminal.

9 Claims, 11 Drawing Sheets

Figure 4:
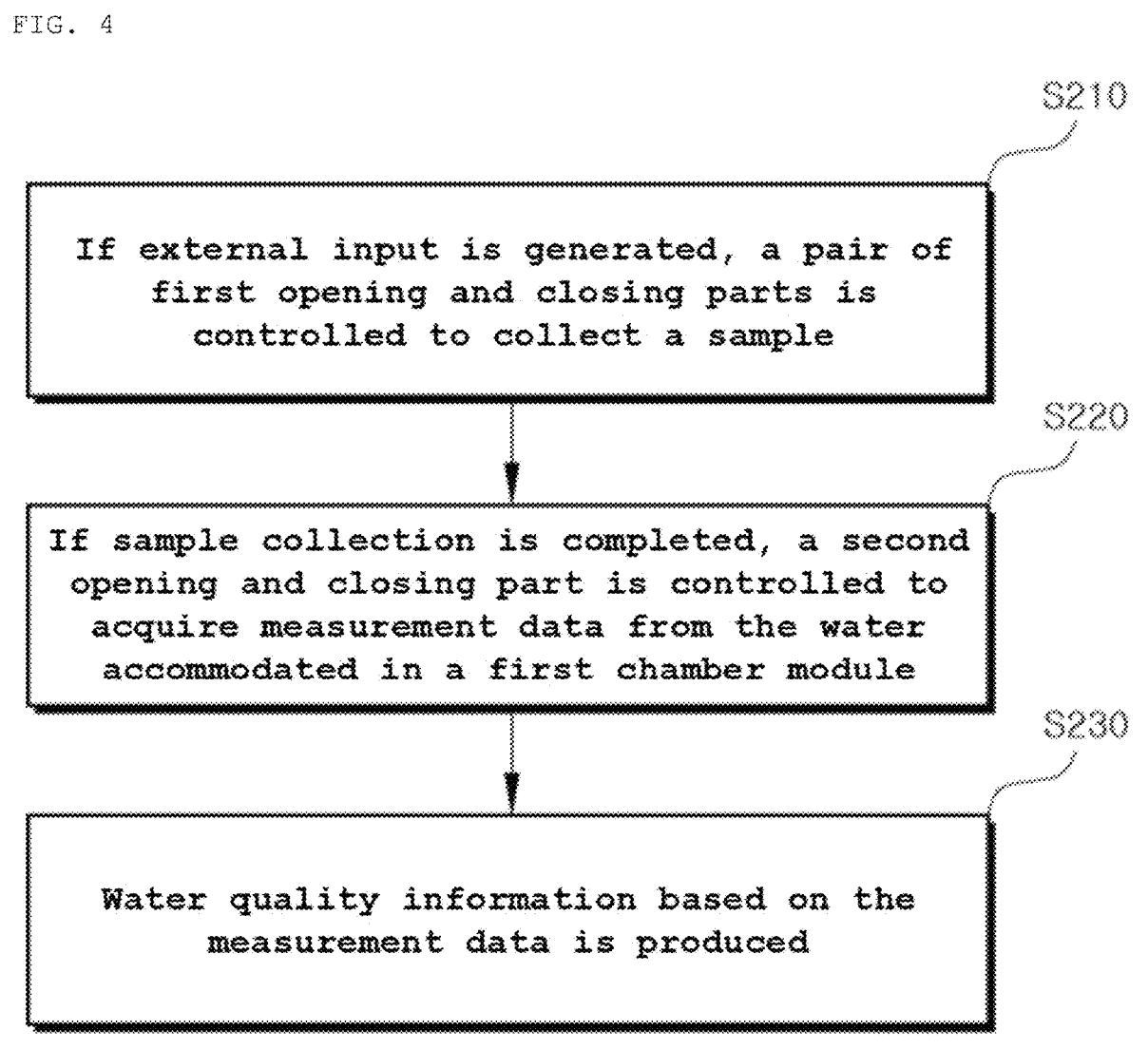

If external input is generated, a pair of
first opening and closing parts is
controlled to collect a sample

S220

If sample collection is completed, a second
opening and closing part is controlled to
acquire measurement data from the water
accommodated in a first chamber module

S230

Water quality information based on the
measurement data is produced

REAL-TIME WATER QUALITY MONITORING DEVICE AND METHOD

CROSS REFERENCE TO RELATED APPLICATION OF THE DISCLOSURE

The present application claims the benefit of Korean Patent Application No. 10-2023-0133303 filed in the Korean Intellectual Property Office on Oct. 6, 2023, the entire contents of which are incorporated herein by reference.

BACKGROUND OF THE DISCLOSURE

Field of the Disclosure

The present disclosure relates to a real-time water quality monitoring device and method, more specifically to a real-time water quality monitoring device and method that is capable of making use of a sample collected in real time.

Background of the Related Art

The human body is made up of over 70% water, and accordingly, water is necessary for the survival of the body. As activities of humans increase, however, various types of environmental pollution occur, and among them, a degree of water pollution is serious.

This results in high distrust of tap water used in people's daily lives, and therefore, there is a need to monitor tap water quality in real time.

However, a water quality manager (inspector) has to visit a place where a pipe is installed to directly collect a sample from water flowing along the pipe. As a result, it is difficult to perform real-time water quality monitoring at a desired time.

To monitor a quality of water flowing along the pipe, besides, a water quality measurement instrument is submerged in water to acquire water quality data, and in this case, since a tip of the water quality measurement instrument is made of a fragile material such as quartz, the tip may be likely to be damaged or broken due to the force generated from the flow of water.

Therefore, there is a need to develop a real-time water quality monitoring technology capable of in real time monitoring water flowing along a pipe at a desired time.

PRIOR ART LITERATURE

Patent Literature (Patent literature 0001) Korean Patent No. 10-2202027 (Issued on Jan. 6, 2021)

SUMMARY OF THE DISCLOSURE

Accordingly, the present disclosure has been made in view of the above-mentioned problems occurring in the related art, and it is an object of the present disclosure to provide a real-time water quality monitoring device and method that is capable of allowing some of water flowing to be collected as a sample at a desired time (specific time) through chamber modules bypass-connected to a pipe module to acquire measurement data related to water quality so that a water quality manager does not need to visit a place where the pipe module is installed to directly collect a sample, thereby improving work efficiency and monitoring the water quality based on the collected sample in real time.

To accomplish the above-mentioned objects, according to one aspect of the present disclosure, there is provided a real-time water quality monitoring device including: a pipe module having the shape of a pipe along which water as a fluid flows; a first chamber module connected to the pipe module and having a pair of first opening and closing parts openable and closable according to a control signal so that in a state where the pair of first opening and closing parts is open, the first chamber module provides a path formed in the internal space thereof to flow the water therealong, and in a state where the pair of first opening and closing parts is closed, the first chamber module accommodates the water therein and collects the water as a sample; a second chamber module connected to the first chamber module through a second opening and closing part openable and closable so that if the second opening and closing part is open in the state where the pair of first opening and closing parts is closed, the second chamber module acquires measurement data related to water quality from the water accommodated in the first chamber module by means of a water quality measurement instrument mounted therein; and a control module for generating the control signal according to an external input, producing water quality information using the measurement data, and transmitting the water quality information to at least one predetermined management terminal.

To accomplish the above-mentioned objects, according to another aspect of the present disclosure, there is provided a real-time water quality monitoring method including the steps of: if an external input is generated, allowing a pair of first opening and closing parts of a first chamber module connected to a pipe module to be closed according to a control signal to collect the water accommodated in the first chamber module as a sample; if a second opening and closing part is open in the state where the pair of first opening and closing parts is closed, acquiring measurement data related to water quality from the water accommodated in the first chamber module through a water quality measurement instrument mounted in a second chamber module connected to the first chamber module through the second opening and closing part; producing water quality information using the measurement data; and transmitting the water quality information to at least one predetermined management terminal.

BRIEF DESCRIPTION OF THE DRAWINGS

The above and other objects, features and advantages of the present disclosure will be apparent from the following detailed description of the preferred embodiments of the disclosure in conjunction with the accompanying drawings, in which:

FIG. 4 is a flowchart showing a real-time water quality monitoring method according to the present disclosure;

DETAILED DESCRIPTION OF THE PREFERRED EMBODIMENTS

Figure 1:
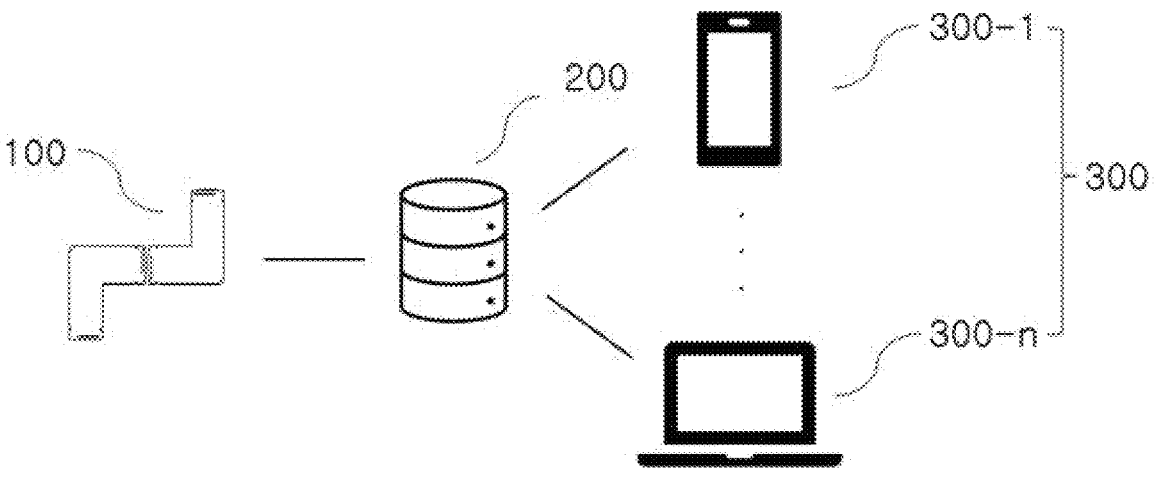
FIG. 1 is a block diagram showing a network structure of a real-time water quality monitoring system according to the present disclosure.

Objects, characteristics, and advantages of the present disclosure will be more clearly understood from the detailed description as will be described below and the attached drawings. Before the present disclosure is disclosed and described, it is to be understood that the disclosed embodiments are merely exemplary of the disclosure, which can be embodied in various forms. Therefore, specific structural and functional details disclosed herein are not to be interpreted as limiting, but merely as a basis for the claims and as a representative basis for teaching one of ordinary skill in the art to variously employ the present disclosure in virtually any appropriately detailed structure.

Terms used in this application are used to only describe specific exemplary embodiments and are not intended to restrict the present disclosure. An expression referencing a singular value additionally refers to a corresponding expression of the plural number, unless explicitly limited otherwise by the context. In the entire specification, when a certain portion "comprises and/or includes" a certain component, this indicates that the other components are not excluded and may be further included unless specially described otherwise. A term "and/or" includes a combination of a plurality of relevant and described items or any one of a plurality of related and described items. Terms, such as "the first", and "the second", may be used to describe various elements, but the elements should not be restricted by the terms. The terms are used to only distinguish one element from the other element. For example, a first element may be named a second element without departing from the scope of the present disclosure.

All terms used herein, including technical or scientific terms, unless otherwise defined, have the same meanings which are typically understood by those having ordinary skill in the art. The terms, such as ones defined in common dictionaries, should be interpreted as having the same meanings as terms in the context of pertinent technology, and should not be interpreted as having ideal or excessively formal meanings unless clearly defined in the specification.

In the description, the same reference numerals will be used to describe the same components and an overlapped description of the same components will be omitted. The terms "parts" or "modules", as used herein, are intended to refer to a hardware component such as field-programmable gate array (FPGA) or application specific integrated circuit (ASIC), or a combination thereof, which executes given functions. However, the terms "parts" or "modules" are not limited to the software or hardware component. The "parts" or "modules" may be configured to be in a storage medium addressable or to play one or more processors. Accordingly, for example, the term "parts" or "modules" may include components such as software components, object-oriented software components, class components, and task components, processes, functions, attributes, procedures, sub-routines, segments of program codes, drivers, firmware, micro-codes, circuits, data, database, data structures, tables, arrays, and variables. The functions provided by the components and the "parts" or "modules" may be combined to those provided by smaller components and "parts" or "modules" or separated into additional components or "parts" or "modules".

When it is said that one element is described as being "connected" or "coupled" to the other element, one element may be directly connected or coupled to the other element, but it should be understood that the two elements are indirectly connected to each other by means of a wireless communication network.

In the description, when it is said that one portion is described as "includes" any component, one element further may include other components unless no specific description is suggested.

In the description, when it is said that one member is located "above" another member, it means that one member may come into contact with another member as well as yet another member may exist between the two members.

Terms, such as the first, and the second, may be used to describe various elements, but the elements should not be restricted by the terms.

An expression referencing a singular value additionally refers to a corresponding expression of the plural number, unless explicitly limited otherwise by the context.

Identification symbols on steps are used for the convenience of the description, and they do not mean the order of the steps. The steps may be differently carried out from the described order unless a specific order is described. That is, the steps may be carried out in the same order as described, carried out at the same time, or carried out in the opposite order to that described.

The terms as will be discussed later are defined as follows.

A term 'server' as used herein, which represents a terminal of a service provider for providing a real-time water quality monitoring service based on a platform and/or web page, may include various devices capable of executing computing processing. In this case, the server of the present disclosure that performs communication with an external device and information processing may include an application server, a computing server, a database server, a file server, a game server, a mail server, a proxy server, a web server, and the like.

Further, the server of the present disclosure may include all kinds of devices, such as a computer, a portable terminal, and the like, and otherwise, the server may be provided in the form of any one of them, without being limited thereto.

In this case, for example, the computer may include a laptop, a desktop, a tablet PC, a slate PC, and the like, which have a web browser built thereon.

For example, the portable terminal, which is a wireless communication device ensuring portability and mobility, may include all types of handheld wireless communication devices, such as a Personal Communication System (PCS), a Global System for Mobile communications (GSM), a Personal Digital Cellular (PDC), a Personal Handyphone System (PHS), a Personal Digital Assistant (PDA), an International Mobile Telecommunication (IMT)-2000, a Code Division Multiple Access (CDMA)-2000, W-CDMA, a Wireless Broadband Internal (WiBro) terminal, a smartphone, and the like and wearable devices, such as a watch, a ring, a bracelet, an anklet, a necklace, glasses, a contact lens, a head-mounted device (HMD), and the like.

Hereinafter, explanations of operating principle and embodiments of the present disclosure will be given with reference to the attached drawings.

FIG. 1 is a block diagram showing a network structure of a real-time water quality monitoring system according to the present disclosure.

Referring to FIG. 1, a real-time water quality monitoring system 10 (hereinafter, referred to as 'water quality monitoring system') according to the present disclosure includes a water quality monitoring device 100, a server 200, and at least one management terminal 300.

The water quality monitoring device 100 is a device that is configured to allow a water quality manager to monitor water quality in real time at a desired time so that a worker does not need to visit a place where a pipe is installed to directly collect a sample, and in this case, the water quality monitoring device 100 easily collects a sample through at least one or more chamber modules bypass-connected to a pipe module in such a way as to have no interrupt in the flow of water along the pipe module.

That is, if the manager makes a request for water quality measurement at a desired time through a specific management terminal, the water quality monitoring device 100 collects the sample according to the request of the manager and acquires measurement data based on the sample.

After that, the water quality monitoring device 100 produces water quality information through the acquired measurement data and transmits the water quality information, through the server 200, to the specific management terminal 300 through which the water quality measurement is requested and to at least one management terminal 300.

The water quality monitoring device 100 may be located on various regions and/or places where pipe modules are installed, respectively, and therefore, at least one or more water quality monitoring devices 100 may be provided, without being limited in number. To distinguish the water quality monitoring devices 100 form one another, however, identifiers, identification codes, registration numbers, etc. may be applied to them.

The server 200 maps the water quality monitoring device 100 that is requested to monitor water quality by the specific management terminal among one at least or more management terminals 300 with at least one management terminal 300 possessed by the manager of the corresponding water quality monitoring device 100 and thus registers the at least one management terminal 300 for the water quality monitoring device 100. As a result, a water quality monitoring service is smoothly executed. In this case, as mentioned above, the water quality monitoring devices 100 are located on various regions and/or places, and accordingly, at least one or more management terminals 300 are mapped and registered differently for the water quality monitoring devices 100. That is, the managers for the water quality monitoring devices 100 may be different from one another.

After that, if the server 200 receives a water quality measurement request through the water quality monitoring device 100 from the specific management terminal, the server 200 checks the water quality monitoring device 100 mapped with the specific management terminal according to the water quality measurement request and makes a request to allow the water quality monitoring device 100 to perform water quality measurement.

Further, if the server 200 receives the water quality information from the water quality monitoring device 100, the server 200 transmits the received water quality information to the at least one predetermined management terminal 300 for the water quality monitoring device 100. In this case, the server 200 transmits the water quality information as received, and otherwise, the server 200 processes the water quality information so that the manager visually checks the water quality information easily through his or her management terminal. In this case, the water quality information includes information of at least one among a time point where water quality measurement is performed, measurement data, pollutants, and a degree of water pollution.

Further, the server 200 produces analysis information by using the water quality information of the water quality monitoring device 100 that is accumulated and stored over a given period of time and transmits the produced analysis information to at least one management terminal 300. In this case, the analysis information includes change information of at least one of the measurement data, the pollutants, and the degree of water pollution. To do this, the server 200 has an artificial intelligence-based pre-trained model for producing the analysis information.

Further, at least one or more management terminals 300-1 to 300-$n$ are terminals possessed by the managers corresponding to the water quality monitoring device 100, and in this case, a plurality of management terminals may be mapped with one water quality monitoring device 100. In this case, the terminals are possessed by managers, for the convenience of the description, but of course, they may be possessed by the persons concerned, the persons in charge, and workers or located in management agencies, the agencies concerned, and the agencies in charge.

If the at least one or more management terminals 300-1 to 300-$n$ receive the water quality information or the analysis information from the server 200, they display the received information on their display module to allow the corresponding managers to visually check the information.

In this case, the management terminal 300 includes a computer, an Ultra Mobile PC (UMPC), a net-book, Personal Digital Assistants (PDA), a portable computer, a web tablet, a wireless phone, a mobile phone, a smart phone, a pad, a smart watch, a wearable terminal, an e-book, a Portable Multimedia Player (PMP), a portable game machine, a navigation device, a black box, a digital camera, and other mobile communication terminals, which install a plurality of application programs (that is, applications) as desired by the manager and execute the applications. That is, THE at least one or more management terminals 300-1 to 300-$n$ are provided to various forms, without being limited in number, kind, and shape.

Figure 2:
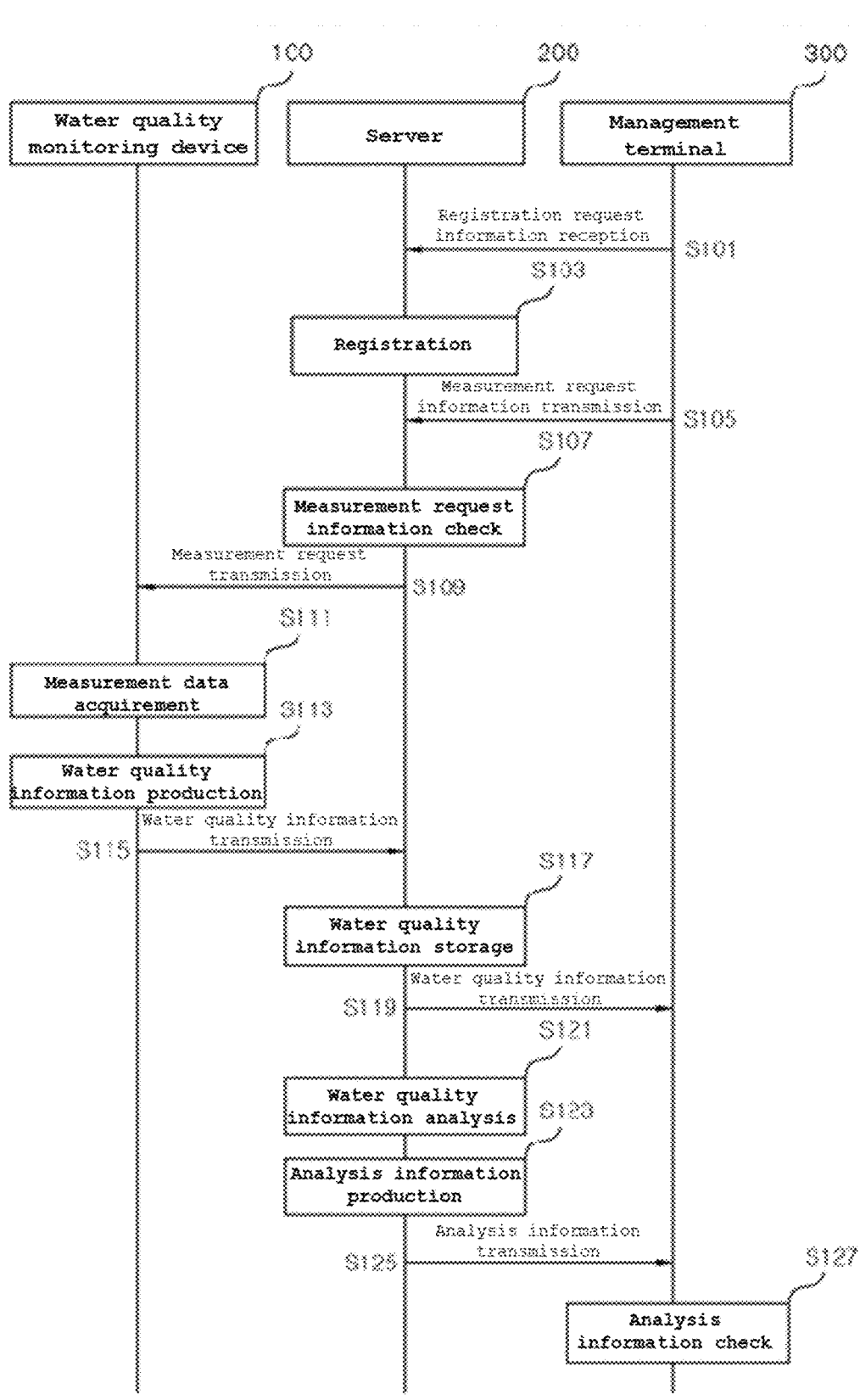
FIG. 2 is a flowchart showing operations of the real-time water quality monitoring system according to the present disclosure.

FIG. 2 is a flowchart showing operations of the real-time water quality monitoring system according to the present disclosure.

Referring to FIG. 2, the management terminal 300 transmits registration request information including information of the management terminal 300 and information of the water quality monitoring device 100 to the server 200 to allow the management terminal 300 and the water quality monitoring device 100 managed by the management terminal 300 to be matchedly registered on the server 200 (Step S101). In this case, the corresponding water quality monitoring device 100 may be managed by at least one or more management terminals, and accordingly, the management terminal 300 transmits the registration request information including the information of other management terminals managing the corresponding water quality monitoring device 100, and otherwise, the respective management terminals managing the corresponding water quality monitoring device 100 individually transmit the registration request information.

Next, the server 200 matches the management terminal 300 with the corresponding water quality monitoring device 100 according to the information included in the registration request information received from the management terminal 300 and stores the matched result (Step S103).

Next, the management terminal 300 transmits measurement request information to the server 200 according to an input signal generated by the manager (Step S105). In this case, the measurement request information includes the information of the corresponding water quality monitoring device 100 disposed in the region and/or place to be desired to monitor water quality in real time among the plurality of water quality monitoring devices 100, and the corresponding water quality monitoring device 100 is selected by the manager.

Next, the server 200 checks the corresponding water quality monitoring device 100 to be desired to measure water quality in real time according to the measurement request information received at the step S105 (Step S107) and transmits a measurement request to the corresponding water quality monitoring device 100 to allow the corresponding water quality monitoring device 100 to perform real-time water quality measurement (Step S109).

After that, the corresponding water quality monitoring device 100 acquires measurement data according to the measurement request received at the step S109 (Step S111), produces the measurement data-based water quality information (Step S113), and transmits the water quality information to the server 200 (Step S115).

Next, the server 200 stores the water quality information received at the step S115 (Step S117) and transmits the water quality information to the management terminal 300 that transmits the measurement request information at the step S105 (Step S119).

Further, the steps S105 to S119 may be repeatedly performed, and accordingly, the server 200 accumulates and stores the water quality information stored. In this case, the server 200 analyzes the water quality information accumulated and stored every set periods of time or according to the request of the management terminal 300 (Step S121) and produces analysis information based on the analyzed result (Step S123).

Next, the server 200 transmits the analysis information produced at the step S123 to the management terminal 300 (Step S125), and the management terminal 300 receives the analysis information and displays the analysis information on a display module to allow the manager to visually check the analysis information (Step S127).

While the steps S119 and S125 are being performed, further, if other predetermined management terminals managing the corresponding water quality monitoring device 100 exist, the server 200 transmits the water quality information or the analysis information to other predetermined management terminals as well as the management terminal 300 making a request for the information.

However, FIG. 2 shows just an exemplary embodiment, and accordingly, another embodiment may be provided so that the water quality monitoring device 100 acquires measurement data like the step S111 and transmits the measurement data as acquired to the server 200, and the server 200 produces the water quality information based on the measurement data.

Hereinafter, a configuration and operations of the water quality monitoring device 100 will be explained.

Figure 3:
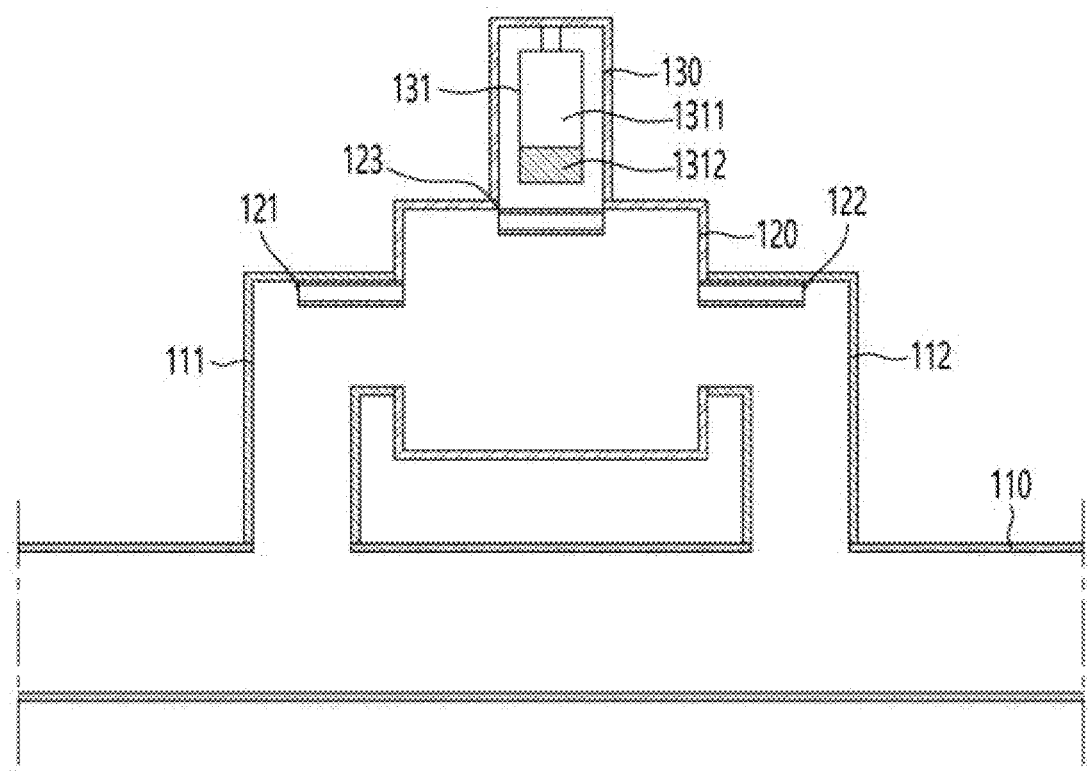
FIG. 3 is a sectional view showing a water quality monitoring device according to the present disclosure.

FIG. 3 is a sectional view showing the real-time water quality monitoring device according to the present disclosure.

Referring to FIG. 3, the real-time water quality monitoring device 100 (hereinafter, referred to as 'water quality monitoring device') according to the present disclosure includes a pipe module 110, a first chamber module 120, a second chamber module 130, and a control module 140.

The pipe module 110 has the shape of a pipe along which water flows.

Further, the first chamber module 120 is bypass-connected to the pipe module 110 by means of a pair of connection ducts 111 and 112. The first chamber module 120 has a pair of first opening and closing parts 121 and 122 disposed on water inlet and outlet ends in such a way as to be openable and closable according to control signals. In a state where the first opening and closing parts 121 and 122 are open, the first chamber module 120 has a path formed therein to flow the water therealong, and in a state where the first opening and closing parts 121 and 122 are closed, the first chamber module 120 accommodates the water therein and collects the water as a sample.

Further, the second chamber module 130 is connected to the first chamber module 120 through a second opening and closing part 123, and in the state where the first opening and closing parts 121 and 122 are closed, the second opening and closing part 123 is open so that the second chamber module 130 acquires the measurement data related to water quality from the water accommodated in the first chamber module 120 by means of a water quality measurement instrument 131 mounted therein.

In this case, the water quality measurement instrument 131 of the second chamber module 130 includes a body 1311 and a tip 1312 as a measuring portion disposed on the lower portion of the body 1311.

Further, for example, the first opening and closing parts 121 and 122 and the second opening and closing part 123 have the shapes of plates, but they may not be limited in shapes, fastening ways, or operating ways. Besides, the first opening and closing parts 121 and 122 and the second opening and closing part 123 have given volumes to increase the level of the surface of water accommodated in the first chamber module 120 and the second chamber module 130.

Furthermore, even though not shown in FIG. 3, the control module 140 is provided to measure the water quality in real time, and the control module 140 generates control signals according to external inputs, produces water quality information using the measurement data acquired through the control signals, and transmits the water quality information to the at least one predetermined management terminal.

According to an embodiment of the present disclosure, first, if the second opening and closing part 123 is open, the control module 140 moves the water quality measurement instrument 131 toward the first chamber module 120 to allow the water quality measurement instrument 131 to acquire the measurement data, and according to another embodiment of the present disclosure, if the water accommodated in the first chamber module 130 moves to the second chamber module 130 according to the change in volume of the internal space of the first chamber module 120, the control module 140 allows the water quality measurement instrument 131 to acquire the measurement data.

That is, the control module 140 moves the water quality measurement instrument 131 mounted in the second chamber module 130 to acquire the measurement data from the water accommodated in the first chamber module 120, and otherwise, the control module 140 acquires the measurement data from the water that has moved to the second chamber module 130 according to the increase of the level of the surface of water accommodated in the first chamber module 120.

In this case, the level of the surface of water accommodated in the first chamber module 120 increases as the second opening and closing part 123 is open and thus submerged in the water accommodated in the first chamber module 120.

In this case, the control module 140 allows the first chamber module 120 to accommodate the water therein in the state where the first opening and closing parts 121 and 122 are closed and then allows the second chamber module 130 to acquire the measurement data in the state where the second opening and closing part 123 is open. Otherwise, according to structural features of the second chamber module 130 where the second chamber module 130 is slant with respect to the surface of the ground, the water is accommodated in the second chamber module 130, and if the second opening and closing part 123 is open, the surface of water is parallel to the surface of the ground to allow the tip 1312 of the water quality measurement instrument 131 to come into contact therewith.

In another embodiment of the present disclosure, the control module 140 maintains a state where the tip 1312 of the water quality measurement instrument 131 is submerged in the water accommodated in the first chamber module 120 at an nth time point, in the state where the second opening and closing part 123 is closed, and allows the accommodated water at an n+1th time point in the state where the second opening and closing part 123 is open to be mixed with the accommodated water at the nth time point to produce mixed water so that the control module 140 allows the measurement data based on the mixed water to be acquired through the water quality measurement instrument 131.

In this case, the second chamber module 130 is kept in a state where the tip 1312 of the water quality measurement instrument 131 is submerged in the mixed water accommodated therein.

To do this, the control module 140 first closes the first opening and closing part 122 disposed on the outlet end to introduce the water in the internal space of the first chamber module 120 and next closes a portion of the first opening and closing part 121 disposed on the inlet end and simultaneously opens a portion of the second opening and closing part 123 so that the water is accommodated in the first chamber module 120 and the second chamber module 130.

Further, the control module 140 completely closes the second opening and closing part 123 after a predetermined time passes and submerges the tip 1312 of the water quality measurement instrument 131 in the water accommodated in the second chamber module 130 to acquire the measurement data.

Furthermore, even though not shown in FIG. 3, the water quality monitoring device 100 may include a communication module (not shown) and a storage module (not shown). FIG. 3 shows the state where the first chamber module is disposed on top of the pipe module and the second chamber module on top of the first chamber module, but the present disclosure may not be limited therein. The pipe module, the first chamber module, and the second chamber module may not be limited in their position relation. For example, reverse arrangements may be made around the pipe module, and otherwise, the first chamber module may be disposed on the underside of the pipe module, while the second chamber module is being disposed on top of the first chamber module.

In specific, the communication module transmits and receives at least a piece of information or data to and from at least one device/terminal. In this case, at least one device/terminal represents a device/terminal that desires to receive the real-time water quality monitoring service as well as the server 200 and/or at least one management terminal 300, without being limited in kind and shape.

Further, the communication module performs communication with other devices excepting the above-mentioned device/terminal and transmits and receives wireless signals through a communication network based on a wireless internet technology.

The wireless internet technology includes Wireless LAN (WLAN), Wireless-Fidelity (Wi-Fi), Wi-Fi Direct, Digital Living Network Alliance (DLNA), Wireless Broadband (WiBro), World Microwave (WiMAX), High Speed interoperability for Access Downlink Packet Access (HSDPA), High Speed Uplink Packet Access (HSUPA), Long Term Evolution (LTE), LTE-Advanced (LTE-A), and the like, and the water quality monitoring device 100 transmits and receives data according to at least one wireless internet technology in the range including internal technologies not mentioned above.

To allow short-range wireless communication to be performed, the communication module performs the short-range wireless communication using at least one of Bluetooth™, Radio Frequency Identification (RFID), Infrared Data Association (IrDA), Ultra-wideband (UWB), ZigBee, Near Field Communication (NFC), Wi-Fi, Wi-Fi Direct, and Wireless Universal Serial Bus (USB). Such wireless local-area networks support wireless communication among the water quality monitoring device 100, the server 200 and/or the at least one management terminal 300. In this case, the wireless local-area networks may be wireless personal area networks.

Further, the storage module stores at least one (algorithm) for providing the real-time water quality process monitoring service or data of a program reproducing the process. Besides, the storage module stores processes for executing other operations, without being limited thereto.

Moreover, the storage module stores a plurality of application programs or applications operating in the water quality monitoring device 100 and data and commands for the operations of the water quality monitoring device 100. Some of the application programs are downloaded from an external server through wireless communication. Further, the application programs are operated (or executed) by at least one processor stored in at least one memory disposed in the storage module on the water quality monitoring device 100 through the control module 140.

At least one memory includes at least storage medium among a flash memory, hard disc type memory, a multimedia card micro type memory, a card type memory (e.g., SD or XD memory), a Random Access Memory (RAM), a Static RAM (SRAM), a Read-Only Memory (ROM), an Electrically Erasable Programmable ROM (EEPROM), a PROM, a magnetic memory, a magnetic disc, and an optical disc. Further, the memory stores information temporarily, permanently, semi-permanently and is built in the storage module or detachable therefrom.

Besides, the storage module interlinks with the external server (including a cloud server).

Further, an explanation of specific operations of the control module 140 will be given below with reference to the attached drawings.

FIG. 4 is a flowchart showing a real-time water quality monitoring method according to an embodiment of the present disclosure.

Referring to FIG. 4, if an external input is generated, the water quality monitoring device 100 allows the pair of first opening and closing parts 121 and 122 disposed on the inlet and outlet ends of the first chamber module 120 bypass-connected to the pipe module 110 to be closed according to the control signal corresponding to the external input to collect the water accommodated therein as a sample (Step S210).

Next, if the sample collection is completed at the step S210, the water quality monitoring device 100 allows the second opening and closing part 123 to be open to acquire measurement data from the water accommodated in the first chamber module 120 (Step S220). In this case, the water quality monitoring device 100 allows the water quality measurement instrument 131 mounted in the second chamber module 130 to acquire the measurement data.

After that, the water quality monitoring device 100 produces water quality information using the measurement data acquired at the step S220 (Step S230) and transmits the water quality information to at least one predetermined management terminal 300.

In the step S220, the water quality measurement instrument 131 moves to acquire the measurement data from the water accommodated in the first chamber module 120, and otherwise, the level of the surface of the water accommodated in the first chamber module 120 increases to allow the water to move to the second chamber module 130 so that the measurement data is acquired from the water accommodated in the second chamber module 130.

Figure 5:
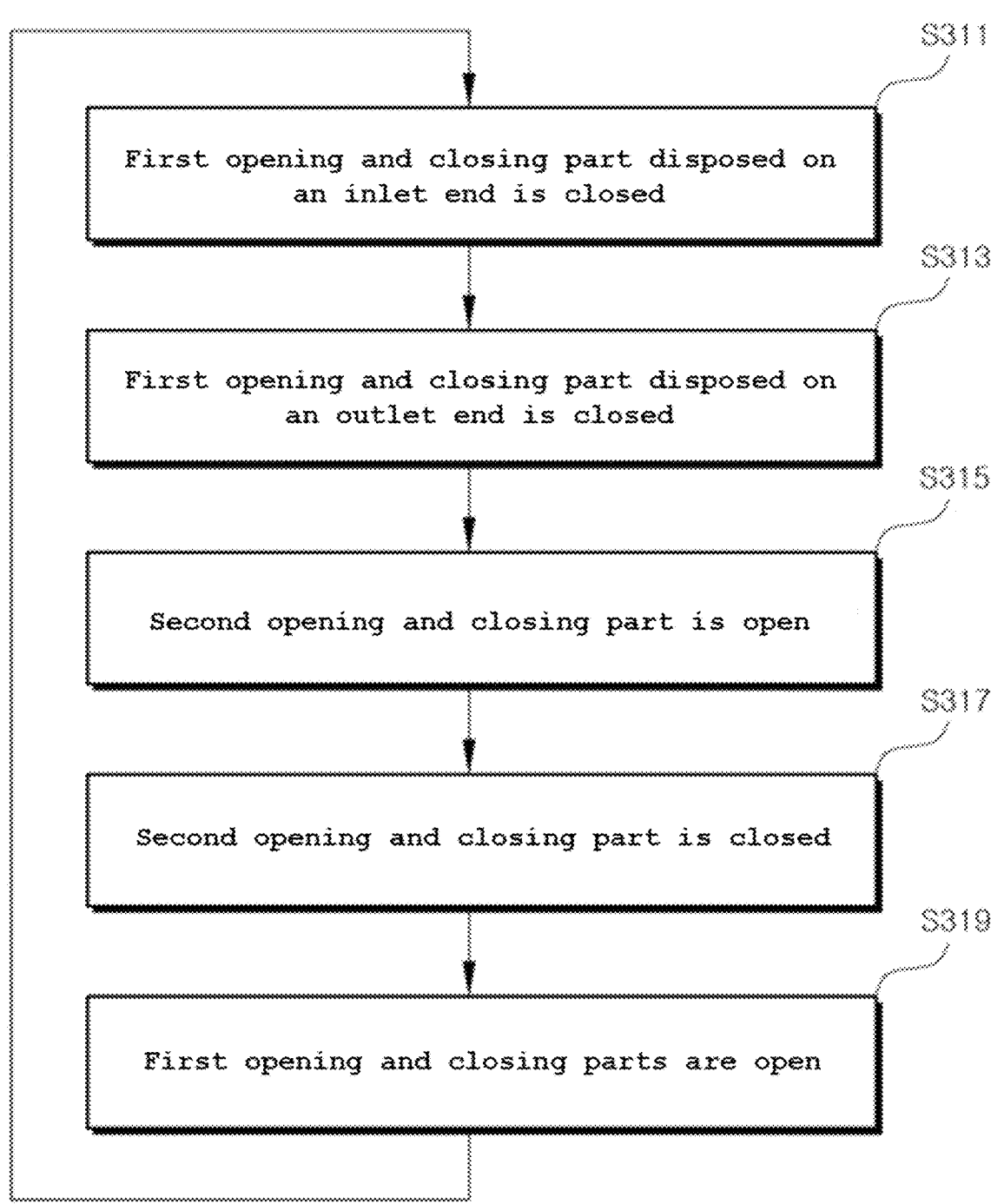
FIG. 5 is a flowchart showing a method for controlling opening and closing operations of first and second opening and closing parts of the real-time water quality monitoring device according to a first embodiment of the present disclosure.

FIG. 5 is a flowchart showing a method for controlling opening and closing operations of the first and second opening and closing parts of the real-time water quality monitoring device according to a first embodiment of the present disclosure.

Referring to FIG. 5, the water quality monitoring device 100 allows the first opening and closing part 122 disposed on the outlet end thereof to be first closed (Step S311) and allows the first opening and closing part 121 disposed on the inlet end thereof to be closed after a predetermined time passes so that the water is accommodated in the first chamber module 120 (Step S313).

Next, the water quality monitoring device 100 allows the second opening and closing part 123 to be open to move the water quality measurement instrument 131 to the interior of the first chamber module 120 so that the measurement data is acquired through the tip 1312 (Step S315).

After that, if the acquirement of the measurement data is completed at the step S315, the water quality monitoring device 100 allows the second opening and closing part 123 to be closed (Step S317) and allows the first opening and closing parts 121 and 122 to be open so that the internal space of the first chamber module 120 is used as a path along which the water flows (Step S319).

The steps S311 to S319 may be repeatedly performed every predetermined periods of time or whenever a control signal is inputted to collect a sample.

Hereinafter, an explanation of the opening and closing operations of the first opening and closing parts 121 and 122 and the second opening and closing part 123 will be given with reference to FIGS. 6A to 6C.

Figure 6A:
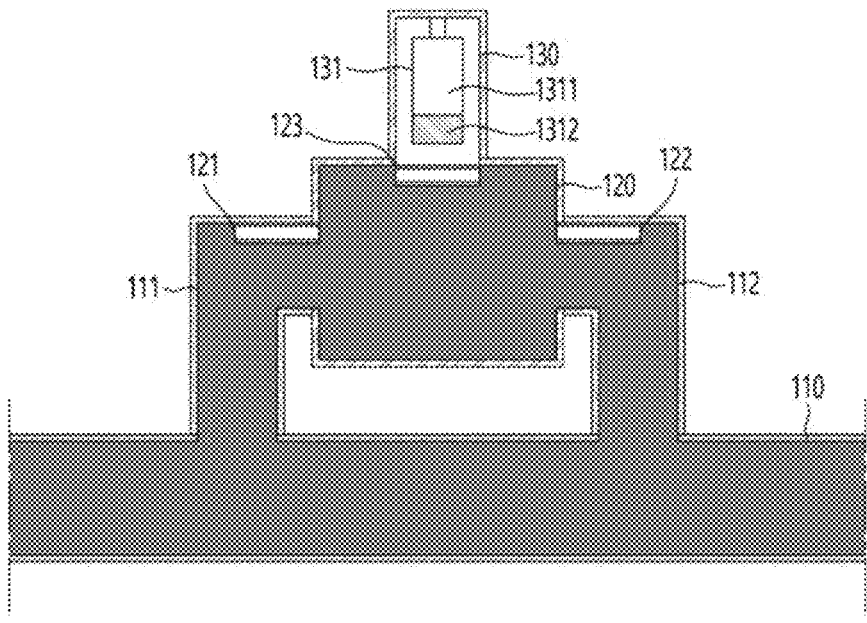
FIGS. 6A, 6B, and 6C are sectional views showing states where the first and second opening and closing parts are opened and closed in the real-time water quality monitoring device according to the first embodiment of the present disclosure.
Figure 6B:
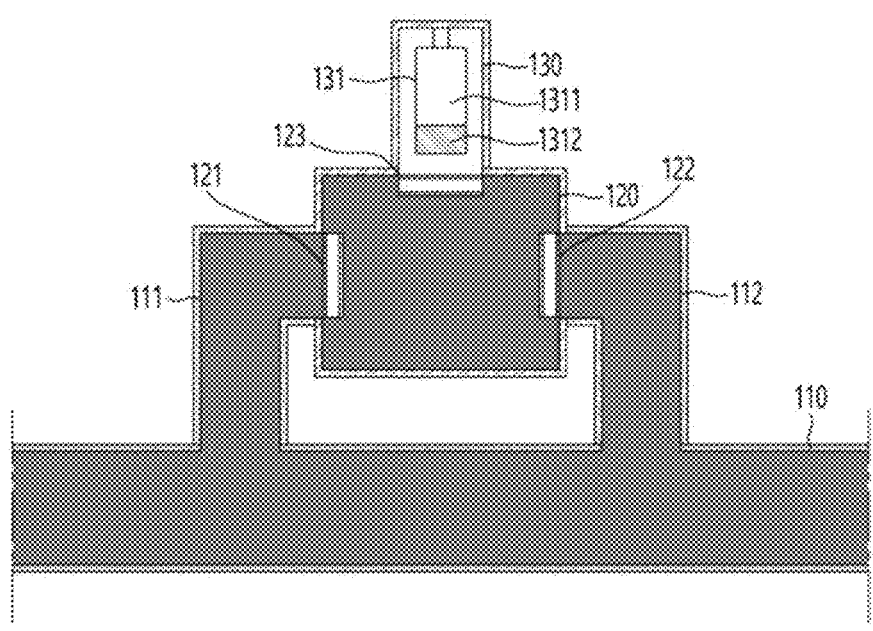
Figure 6C:
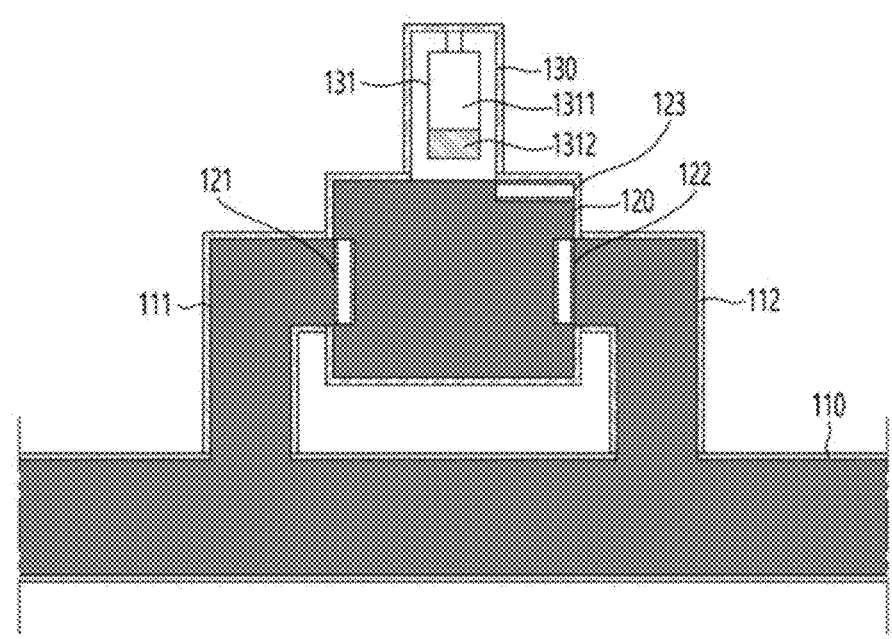

FIGS. 6A to 6C are sectional views showing states where the first and second opening and closing parts are open and closed in the real-time water quality monitoring device according to the first embodiment of the present disclosure.

Referring to FIG. 6A, the water quality monitoring device 100 allows the pair of first opening and closing parts 121 and 122 of the first chamber module 120 to be kept open if no control signal exists in the state where the first chamber module 120 is bypass-connected to the pipe module 110 through the pair of connection ducts 111 and 112, so that the path along which the water flows is formed in the internal space of the first chamber module 120. In this case, the second opening and closing part 123 connecting the first chamber module 120 and the second chamber module 130 to each other is kept closed, which prevents the tip 1312 of the water quality measurement instrument 131 mounted in the second chamber module 130 from being damaged due to the flow of the water.

After that, if the water quality monitoring device 100 receives a control signal from the server 200, the water quality monitoring device 100 allows the pair of first opening and closing parts 121 and 122 to become closed according to the control signal, as shown in FIG. 6B, so that the water is accommodated in the first chamber module 120. Accordingly, the water accommodated in the first chamber module 120 is collected as a sample.

If the sample collection in the first chamber module 120 is completed, as shown in FIG. 6C, the water quality monitoring device 100 allows the second opening and closing part 123 to become open to move the water quality measurement instrument 131 to the interior of the first chamber module 120 so that the measurement data is acquired through the tip 1312.

In this case, the completion of the sample collection is determined according to the level of the surface of the water accommodated in the first chamber module 120. To do this, at least one or more sensors are mounted in the first chamber module 120.

Figure 7:
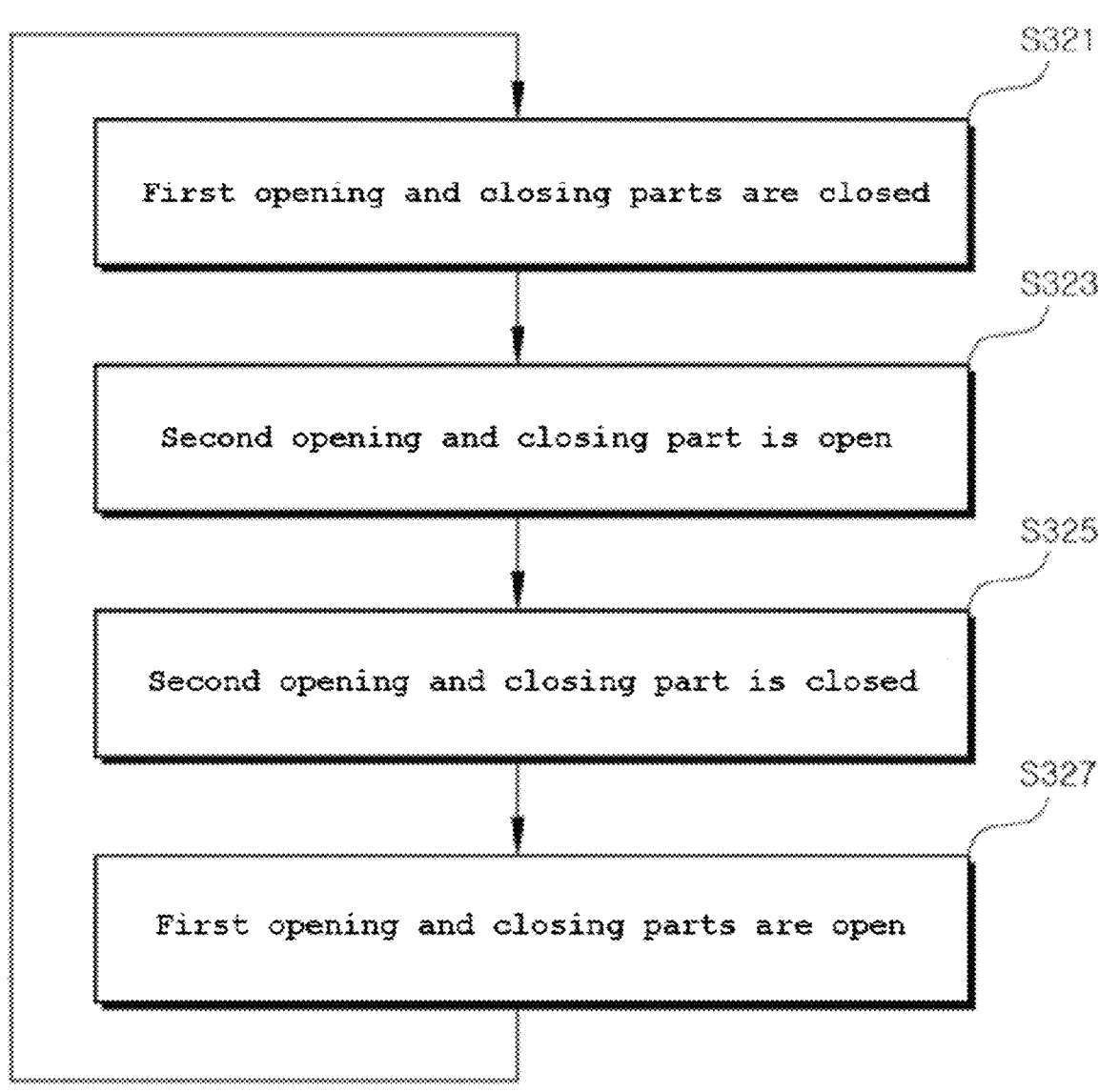
FIG. 7 is a flowchart showing a method for controlling opening and closing operations of first and second opening and closing parts of the real-time water quality monitoring device according to a second embodiment of the present disclosure.

FIG. 7 is a flowchart showing a method for controlling opening and closing operations of the first and second opening and closing parts of the real-time water quality monitoring device according to a second embodiment of the present disclosure.

Specific operations of collecting a sample and controlling the pair of first opening and closing parts 121 and 122 and the second opening and closing part 123 to allow the measurement data to be acquired from the sample collected will be explained.

Referring to FIG. 7, the water quality monitoring device 100 allows the first opening and closing parts 121 and 122 to become closed to accommodate the water in the internal space of the first chamber module 120 so that the water flowing along the internal space of the bypass-connected first chamber module 120 as the path is collected as a sample (Step S321) and then allows the second opening and closing part 123 to become open (Step S323). In this case, as the second opening and closing part 123 becomes open, the water accommodated in the second chamber module 130 is mixed with the water accommodated in the first chamber module 120 in the step S321.

Next, the water quality monitoring device 100 allows the second opening and closing part 123 to become closed after a predetermined time passes so that the mixed water is accommodated in the second chamber module 130 and measurement data is acquired through the tip 1312 of the water quality measurement instrument 131 (Step S325).

After the second opening and closing part 123 has closed or the acquirement of the measurement data has been completed in the step S325, next, the water quality monitoring device 100 allows the first opening and closing parts 121 and 122 to become open so that the internal space of the first chamber module 120 is used as a path along which the water flows (Step S327).

The steps S321 to S327 may be repeatedly performed every predetermined periods of time or whenever a control signal is inputted to collect the sample.

Hereinafter, an explanation of the opening and closing operations of the first opening and closing parts 121 and 122 and the second opening and closing part 123 will be given with reference to FIGS. 8A to 8D.

FIGS. 8A to 8D are sectional views showing states where the first and second opening and closing parts are opened and closed in the real-time water quality monitoring device according to the second embodiment of the present disclosure.

Figure 8A:
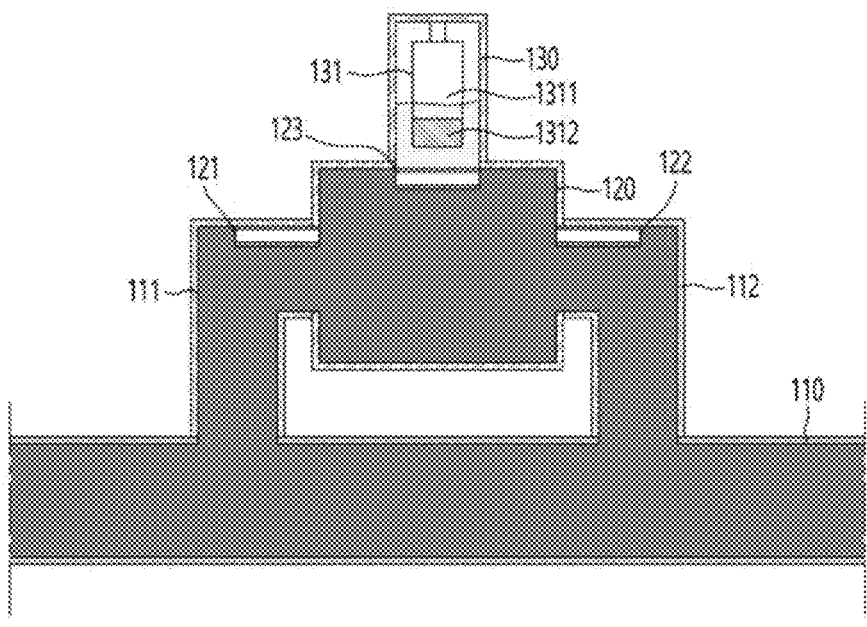
FIGS. 8A, 8B, 8C, and 8D are sectional views showing states where the first and second opening and closing parts are opened and closed in the real-time water quality monitoring device according to the second embodiment of the present disclosure.

Referring to FIG. 8A, the water quality monitoring device 100 allows the pair of first opening and closing parts 121 and 122 of the first chamber module 120 to be kept open if no control signal exists in the state where the first chamber module 120 is bypass-connected to the pipe module 110 through the pair of connection ducts 111 and 112, so that the path along which the water flows is formed in the internal space of the first chamber module 120. In this case, the second opening and closing part 123 connecting the first chamber module 120 and the second chamber module 130 to each other is kept closed, which prevents the tip 1312 of the water quality measurement instrument 131 mounted in the second chamber module 130 from being damaged due to the flow of the water or being contaminated with dust due to the exposure in the air. In this case, the water introduced when the measurement data is acquired at the nth time point is accommodated in the second chamber module 130, and accordingly, the tip 1312 of the water quality measurement instrument 131 is kept submerged in the water. This protects the tip 1312 of the water quality measurement instrument 131.

Figure 8B:
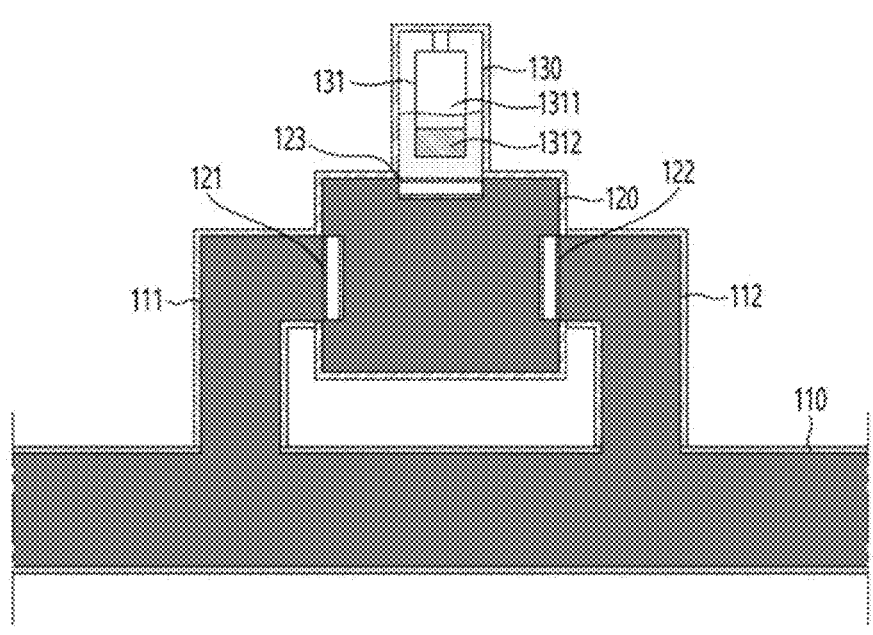
Figure 8C:
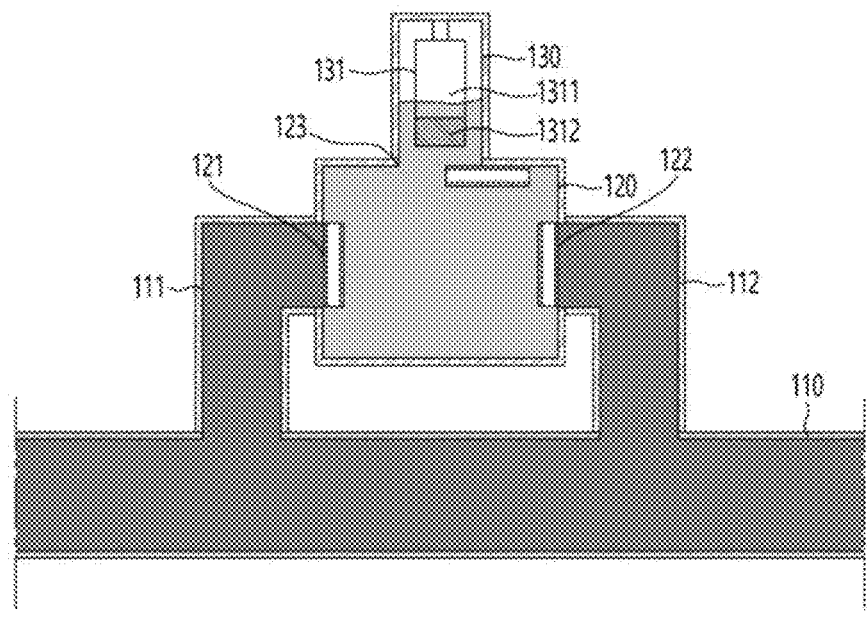

After that, if the water quality monitoring device 100 receives a control signal from the server 200, the water quality monitoring device 100 allows the pair of first opening and closing parts 121 and 122 to become closed according to the control signal, as shown in FIG. 8B, so that the water is accommodated in the first chamber module 120, and next, as shown in FIG. 8C, the water quality monitoring device 100 allows the second opening and closing part 123 to be partially (or fully) open to mix the water accommodated in the first chamber module 120 with the water accommodated in the second chamber module 130.

Figure 8D:
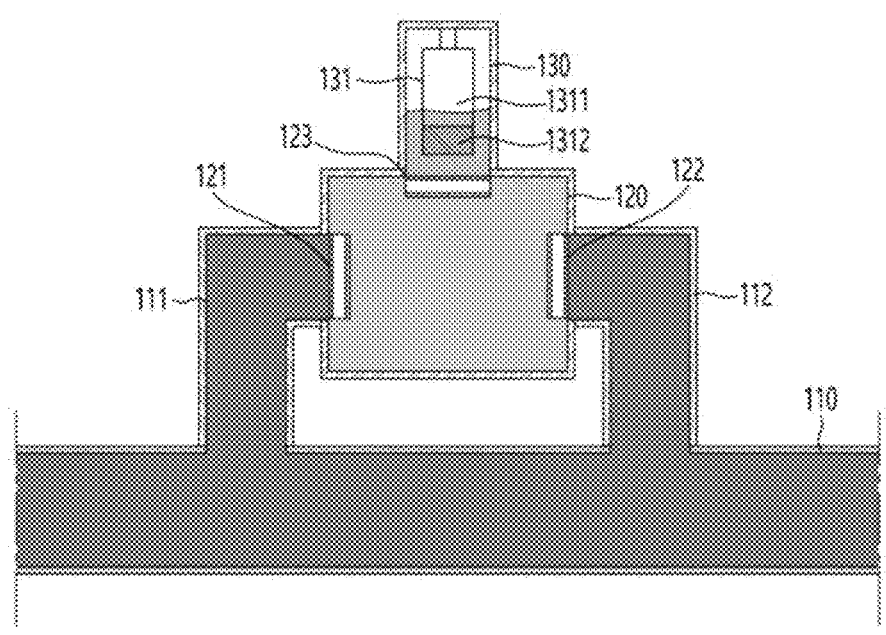

In more detail, as shown in FIG. 8D, the water, which is collected at the nth time point and then accommodated into the second chamber module 130, is mixed with the water introduced at an n+1th time point and accommodated in the first chamber module 120 when the sample is collected at the n+1th time point.

Next, as shown in FIG. 8D, the water quality monitoring device 100 allows the second opening and closing part 123 to become closed after a predetermined time passes so that measurement data is acquired from the water accommodated in the second chamber module 130 through the water quality measurement instrument 131. That is, the water accommodated in the second chamber module 130 is obtained by mixing the water accommodated in the second chamber module 130 as shown in FIG. 8A and the water accommodated in the first chamber module 120 as shown in FIG. 8B when the second opening and closing part 123 becomes open as shown in FIG. 8C. Accordingly, the water accommodated in the second chamber module 130 as shown in FIG. 8D, that is, the water used in acquiring the measurement data is the mixed water at the nth time point and the n+1th time point.

In more detail, the first water is accommodated in the second chamber module 130 so that the second opening and closing part 130 is kept closed to allow the tip 1312 of the water quality measurement instrument 131 to be submerged in the first water, and next, the first opening and closing parts 121 and 122 become closed so that if the second water is accommodated in the first chamber module 120, the second opening and closing part 130 becomes open to allow the measurement data to be acquired through the tip 1312 of the water quality measurement instrument 131 submerged in the mixed water where the first water and the second water are mixed.

As mentioned above, the water quality monitoring device 100 shown in FIGS. 6A to 6C is the same as shown in FIGS. 8A to 8D, but the state where the water is not accommodated in the second chamber module 130 or the state where the water is accommodated in the second chamber module 130 is kept according to the order of controlling the first opening and closing parts 121 and 122 and the second opening and closing part 123.

According to another embodiment of the present disclosure, further, at least one of the first opening and closing parts 121 and 122 and the second opening and closing part 123 has a predetermined volume so that through the opening and closing operation thereof, the level of the surface of the water accommodated in the first chamber module 120 increases toward the second chamber module 130, and accordingly, the measurement data is acquired without moving the water quality measurement instrument 131 mounted in the second chamber module 130 toward the internal space of the first chamber module 120.

According to yet another embodiment of the present disclosure, further, in controlling the pair of first opening and closing parts 121 and 122, the first opening and closing part 121 disposed on the outlet end becomes first closed to allow the water to be introduced in the first chamber module 120, and next, the first opening and closing part 121 disposed on the inlet end becomes partially closed, while the second opening and closing partially open, so that the water is part 123 is being accommodated in the first chamber module 120 and the second chamber module 130, and accordingly, the measurement data is acquired without moving the water quality measurement instrument 131 mounted in the second chamber module 130 toward the internal space of the first chamber module 120. In this case, the reason why the first opening and closing part 121 disposed on the inlet end becomes partially closed and the second opening and closing part 123 is partially closed is the introduction of water prevents the water quality measurement instrument 131 mounted in the second chamber module 130 from being damaged.

As mentioned above, the water quality monitoring device 100 according to the present disclosure moves the water quality measurement instrument 131 to the internal space of the first chamber module 120 to allow the measurement data to be acquired from the water accommodated in the first chamber module 120 or increases the level of the surface of the water accommodated in the first chamber module 120 to allow the water to move to the second chamber module 130 so that the measurement data is acquired from the water accommodated in the second chamber module 130.

In addition to the first and second embodiments of the present disclosure that have been explained with reference to FIGS. 5 to 8D, the first opening and closing parts 121 and 122 and/or the second opening and closing part 123 have given volumes so that the first opening and closing parts 121 and 122 are simultaneously or sequentially closed to collect the sample, and next, the second opening and closing part 123 becomes open and submerged in the water accommodated in the first chamber module 120 as the sample to increase the level of the surface of the water, which allows some of the sample to move to the internal space of the second chamber module 130. As a result, the measurement data is acquired from the water that has moved to the second chamber module 130, without moving the water quality measurement instrument 131 toward the internal space of the first chamber module 120. In the state where some of the sample moves to the internal space of the second chamber module 130, the second opening and closing part 123 is kept open to acquire the measurement data, and otherwise, the second opening and closing part 123 becomes closed to acquire the measurement data. Further, the second chamber module may be located on the bottom of the first chamber module, and if the second opening and closing part 123 becomes open, the water naturally moves to the second chamber module to acquire the measurement data.

FIGS. 3 to 8D show the embodiments where the pair of connection ducts is bypass-connected to the pipe module, but the present disclosure may not be limited to such embodiments. Hereinafter, an explanation of variations of the present disclosure will be given with reference to FIGS. 9A and 9B.

Figure 9A:
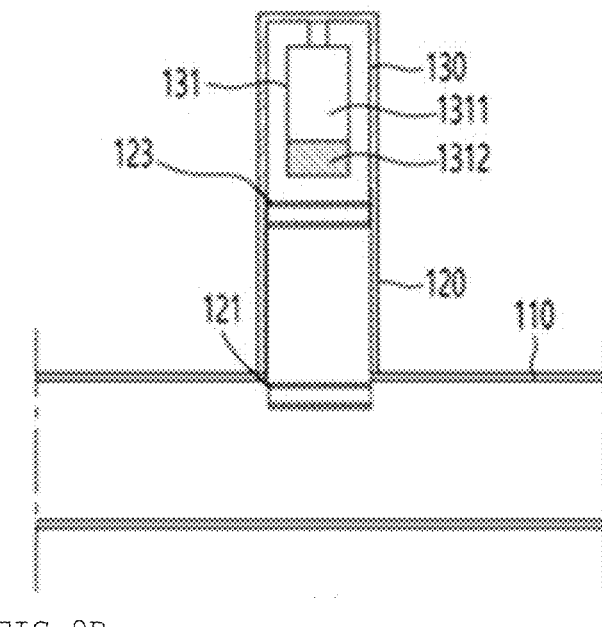
FIGS. 9A and 9B are sectional views showing configurations of real-time water quality monitoring devices according to other embodiments of the present disclosure.
Figure 9B:
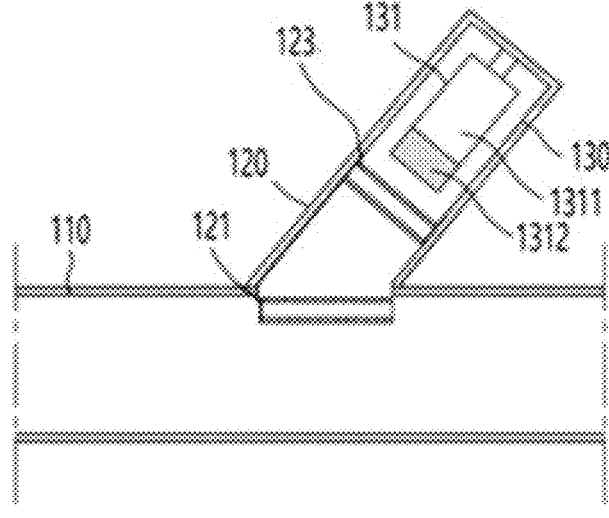

FIGS. 9A and 9B are sectional views showing configurations of real-time water quality monitoring devices according to other embodiments of the present disclosure.

Referring to FIGS. 9A and 9B, a first chamber module 120 and a second chamber module 130 are arranged in a line in such a way as to be branched from a pipe module 110 in a given direction. According to the branched direction, the first chamber module 120 and the second chamber module 130 are branched to the shape of T as shown in FIG. 9A and to the shape of y as shown in FIG. 9B. Further, the branched angle as shown in FIG. 9B is not limited, and FIGS. 9A and 9B show the first chamber module 120 and the second chamber module 130 that are branched upward. However, they may be branched downward, without being limited thereto.

The real-time water quality monitoring device as shown in FIGS. 9A and 9B performs the same operations as those as shown in FIGS. 3 to 8D. In detail, the water quality monitoring device allows a first opening and closing part 121 to be kept open if no control signal exists in the state where the first chamber module 120 is connected to the pipe module 110, so that a path along which water flows is formed in the internal space of the first chamber module 120. In this case, a second opening and closing part 123 connecting the first chamber module 120 and the second chamber module 130 to each other is kept closed, which prevents a tip 1312 of a water quality measurement instrument 131 mounted in the second chamber module 130 from being damaged due to the flow of the water.

After that, if the water quality monitoring device receives a control signal from the server 200, the water quality monitoring device allows the first opening and closing part 121 to become closed according to the control signal so that the water is accommodated in the first chamber module 120. Accordingly, the water accommodated in the first chamber module 120 is collected as a sample.

If the sample collection in the first chamber module 120 is completed, the water quality monitoring device allows the second opening and closing part 123 to become open to move the water quality measurement instrument 131 to the interior of the first chamber module 120 so that the measurement data is acquired through the tip 1312. In this case, the completion of the sample collection is determined according to the level of the surface of the water accommodated in the first chamber module 120. To do this, at least one or more sensors are mounted in the first chamber module 120. If a design where the water does not remain in the second chamber module 130 is made, the operations as shown in FIGS. 6A to 6C are performed, and contrarily, if a design where the water remains in the second chamber module 130 is made, the operations as shown in FIGS. 8A to 8D are performed. If the first chamber module 120 and the second chamber module 130 are branched downward, the water naturally moves to the second chamber module 130 by means of gravity and is mixed with the water pre-remaining in the second chamber module 130, as shown in FIGS. 8A to 8D, so that the water quality measurement is performed with the mixed water.

Under the configuration as shown in FIG. 9B, the water is accommodated in the second opening and closing part 123 slant to the surface of the ground, and if the second opening and closing part 123 becomes open, the surface of the water is parallel with the surface of the ground so that the surface of the water comes into contact with the tip 1312 of the water quality measurement instrument 131. In this case, the water quality measurement is performed using water level drop, without any separate control of the water quality monitoring device.

Further, the water quality monitoring device 100 compares the measurement data acquired through the operations as shown in FIGS. 5 and 7 with the measurement data acquired at the pre-time point, and if a difference greater than a predetermined threshold value between the measurement data occurs, the water quality monitoring device 100 determines that a big change is made. Accordingly, the predetermined period of time for the operations as shown in FIGS. 5 and 7 is automatically adjusted to a period of time shorter than the predetermined period of time. That is, the water quality monitoring device 100 automatically adjusts the predetermined period of time to a predetermined period of time shorter or longer than the predetermined period of time according to the monitored result and y sets the adjusted predetermined period of time as the predetermined period of time for the operations as shown in FIGS. 5 and 7.

As described above, the real-time water quality monitoring device is configured to allow some of the water flowing to be collected as a sample at a desired time (specific time) through the chamber module bypass-connected to the pipe module to acquire the measurement data related to water quality so that a water quality manager does not need to visit a place where a pipe is installed to directly collect a sample, thereby improving work efficiency and monitoring the water quality based on the collected sample in real time.

To allow a computer to read the program as mentioned above to execute the method implemented through the program, the program may include codes to a computer language such as C, C++, JAVA, a machine language, and the like, which can be read by the processor (CPU) of the computer through a device interface of the computer. The code may include a functional code related to functions defining the functions required to execute the method and a control code related to execution procedure required to execute the functions by the processor of the computer according to a given procedure. Further, the code may include a code related to memory reference representing that additional information or medium needed to execute the functions by the processor of the computer is referred at any position (address number) of an internal or external memory of the computer. If the communication with another computer or server located at a remote position is needed to execute the functions by the processor of the computer, the code may further include a code related to communication representing that the processor of the computer communicates with any computer or server through a communication module and the processor of the computer transmits and receives any information or media during communication.

The storage medium may represent a medium storing data semi-permanently and readable by a device, not a medium such as a register, a cash, and a memory, which stores data for a short period of time. In detail, examples of the storage medium include ROM, RAM, CD-ROM, magnetic tape, floppy disc, an optical data storing device, but they may not be limited thereto. That is, the program may be stored in various recording media on various servers to which the computer is accessible or in various recording media on a user's computer. Further, the medium is distributed to a computer system connected through a network and stores the code readable by the computer in a distributed fashion.

The steps of a method or algorithm described in connection with the disclosure herein may be embodied directly in hardware, in a software module executed by a processor, or in a combination of the two. A software module may reside in RAM, ROM, EPROM, EEPROM, flash memory, hard disk, a removable disk, a CD-ROM, or any other form of storage medium known in the art.

While the forgoing examples are illustrative of the principles of the present disclosure in one or more particular applications, it will be apparent to those of ordinary skill in the art that numerous modifications in form, usage and details of implementation can be made without the exercise of inventive faculty, and without departing from the principles and concepts of the disclosure. Accordingly, it is not intended that the disclosure be limited, except as by the claims set forth below.

What is claimed is:

1. A real-time water quality monitoring device comprising:
   a pipe module having the shape of a pipe along which water as a fluid flows;
   a first chamber module connected to the pipe module and having a pair of first opening and closing parts openable and closable according to a control signal so that in a state where the pair of first opening and closing parts is open, the first chamber module provides a path formed in the internal space thereof to flow the water therealong, and in a state where the pair of first opening and closing parts is closed, the first chamber module accommodates the water therein and collects the water as a sample;
   a second chamber module connected to the first chamber module through a second opening and closing part openable and closable so that if the second opening and closing part is open in the state where the pair of first opening and closing parts is closed, the second chamber module acquires measurement data related to water quality from the water accommodated in the first chamber module by means of a water quality measurement instrument mounted therein, wherein the level of the surface of the water accommodated in the first chamber module increases as the second opening and closing part is open and submerged in the water accommodated in the first chamber module; and
   a control module for generating the control signal according to an external input, producing water quality information using the measurement data, and transmitting the water quality information to at least one predetermined management terminal.

2. The real-time water quality monitoring device according to claim 1, wherein after the acquirement of the measurement data, the control module is further configured to close the second opening and closing part and opens the pair of first opening and closing parts so that the water flows again in the first chamber module.

3. The real-time water quality monitoring device according to claim 1, wherein the first chamber module is bypass-connected to the pipe module by means of a pair of connection ducts, and the pair of first opening and closing parts is disposed on water inlet and outlet ends through the pair of connection ducts.

4. A real-time water quality monitoring device comprising:
   a pipe module having the shape of a pipe along which water as a fluid flows;
   a first chamber module connected to the pipe module and having a pair of first opening and closing parts openable and closable according to a control signal so that in a state where the pair of first opening and closing parts is open, the first chamber module provides a path formed in the internal space thereof to flow the water therealong, and in a state where the pair of first opening and closing parts is closed, the first chamber module accommodates the water therein and collects the water as a sample;
   a second chamber module connected to the first chamber module through a second opening and closing part openable and closable so that if the second opening and closing part is open in the state where the pair of first opening and closing parts is closed, the second chamber module acquires measurement data related to water quality from the water accommodated in the first chamber module by means of a water quality measurement instrument mounted therein; and
   a control module for generating the control signal according to an external input, producing water quality information using the measurement data, and transmitting the water quality information to at least one predetermined management terminal,
   wherein first water is accommodated in the second chamber module when the control module keeps the second opening and closing part at a closed state so that a tip of the water quality measurement instrument is kept submerged in the first water, wherein the control module is configured to cause the first opening and closing part to be closed so that when second water to be measured is in the first chamber module, the second opening and closing part opens, and the measurement data is then acquired from mixed water comprised of the first water and the second water.

5. The real-time water quality monitoring device according to claim 4, wherein after the acquirement of the measurement data, the control module is further configured to close the second opening and closing part so that the tip of the water quality measurement instrument remains submerged.

6. The real-time water quality monitoring device according to claim 4, wherein the control module is further configured to close the first opening and closing part disposed on the outlet end and partially closes the first opening and closing part disposed on the inlet end, while partially opening the second opening and closing part, so that the water is introduced in the second chamber module, and the control module is further configured to completely close the first opening and closing part disposed on the inlet end after a predetermined time passes before acquiring the measurement data from the water introduced in the second chamber module.

7. The real-time water quality monitoring device according to claim 4, wherein after the acquirement of the measurement data, the control module is further configured to close the second opening and closing part and open the pair of first opening and closing parts so that the water flows again in the first chamber module.

8. The real-time water quality monitoring device according to claim 4, wherein the first chamber module is bypass-connected to the pipe module by means of a pair of connection ducts, and the pair of first opening and closing parts is disposed on water inlet and outlet ends through the pair of connection ducts.

9. A real-time water quality monitoring method executed by a device comprising a control module, the method comprising the steps of:

using the control module to close a pair of first opening and closing parts of a first chamber module connected to a pipe module to collect the water accommodated in the first chamber module as a sample;

using the control module to open a second opening and closing part in the state where the pair of first opening and closing parts is closed, acquiring measurement data related to water quality from the water accommodated in the first chamber module through a water quality measurement instrument mounted in a second chamber module connected to the first chamber module through the second opening and closing part, wherein the level of the surface of the water accommodated in the first chamber module increases as the second opening and closing part is open and submerged in the water accommodated in the first chamber module;

producing water quality information using the measurement data; and transmitting the water quality information to at least one predetermined management terminal.

\* \* \* \* \*